United States Patent [19]

Musicant et al.

[11] Patent Number: 4,583,527
[45] Date of Patent: Apr. 22, 1986

[54] DISPOSABLE CUSHIONING DEVICE FOR A LARYNGOSCOPE

[76] Inventors: Belmont S. Musicant, 3260 Club Dr., Los Angeles, Calif. 90064; William W. Musicant, 17650 Tarzana St., Encino, Calif. 91316

[21] Appl. No.: 685,075

[22] Filed: Dec. 24, 1984

[51] Int. Cl.$^4$ ............................................. A61B 1/06
[52] U.S. Cl. .................................................... 128/11
[58] Field of Search ...................... 128/11, 10, 15, 16, 128/136

[56] References Cited

U.S. PATENT DOCUMENTS

| | | | |
|---|---|---|---|
| 2,289,226 | 7/1942 | Von Foregger | 128/16 |
| 2,354,471 | 7/1944 | Macintosh | 128/10 |
| 2,646,036 | 7/1953 | Allyn et al. | 128/6 |
| 2,705,492 | 4/1955 | Chandler | 128/136 |
| 3,016,052 | 1/1962 | Zubren | 128/136 |
| 3,124,129 | 3/1964 | Grossberg | 128/136 |
| 3,236,235 | 2/1966 | Jacobs | 128/136 |
| 3,426,749 | 2/1969 | Jephcott | 128/11 |
| 3,507,272 | 4/1970 | Laerdal | 128/16 |
| 3,513,838 | 5/1970 | Foderick et al. | 128/136 |
| 3,598,113 | 8/1971 | Moore et al. | 128/11 |
| 3,766,909 | 10/1973 | Ozbey | 128/11 |
| 3,771,514 | 11/1973 | Huffman et al. | 128/11 |
| 3,864,832 | 2/1975 | Carlson | 128/136 X |
| 4,041,937 | 8/1977 | Diaz | 128/15 |
| 4,295,465 | 10/1981 | Racz et al. | 128/11 |
| 4,350,154 | 9/1982 | Feldbau | 128/136 |
| 4,384,570 | 5/1983 | Roberts | 128/4 |
| 4,406,280 | 9/1983 | Upsher | 128/11 |
| 4,425,909 | 1/1984 | Rieser | 128/16 |
| 4,432,350 | 2/1984 | Breslau et al. | 128/10 |
| 4,437,458 | 3/1984 | Upsher | 128/11 |
| 4,550,717 | 11/1985 | Berger | 128/16 |

FOREIGN PATENT DOCUMENTS 7450 12/1911 United Kingdom .................. 128/15

Primary Examiner—William H. Grieb
Attorney, Agent, or Firm—W. Edward Johanae

[57] ABSTRACT

The present invention is a disposable cushioning device for use in combination with a laryngoscope which includes a handle and a blade. The handle contains a battery which is connected to a first electrical contact pad on the upper surface of the handle. The blade has a lateral shelf which has a top surface, an upright wall and a blade portion extending in a direction opposite to the shelf. The blade portion is curved from its base to its tip which is in the form of a rounded transverse bar of the same width as the blade portion. The base of the blade portion is hinged to the top of the handle. The blade carries an electric lamp which is connected to a second electrical contact pad in the base of the blade portion. The disposable cushioning device is sterilizable and includes an elongated sheath which has a bottom surface and a top surface. The elongated sheath is slidably and removably coupled to the shelf of the blade so that the bottom surface is adjacent to the shelf. The disposable cushioning device also includes an elongated layer of soft pliable plastic material. An adhesive material adheres the elongated layer of soft pliable plastic material to the top surface of the elongated sheath. The disposable cushioning device protects the upper teeth of a patient undergoing an endotracheal intubation.

4 Claims, 7 Drawing Figures

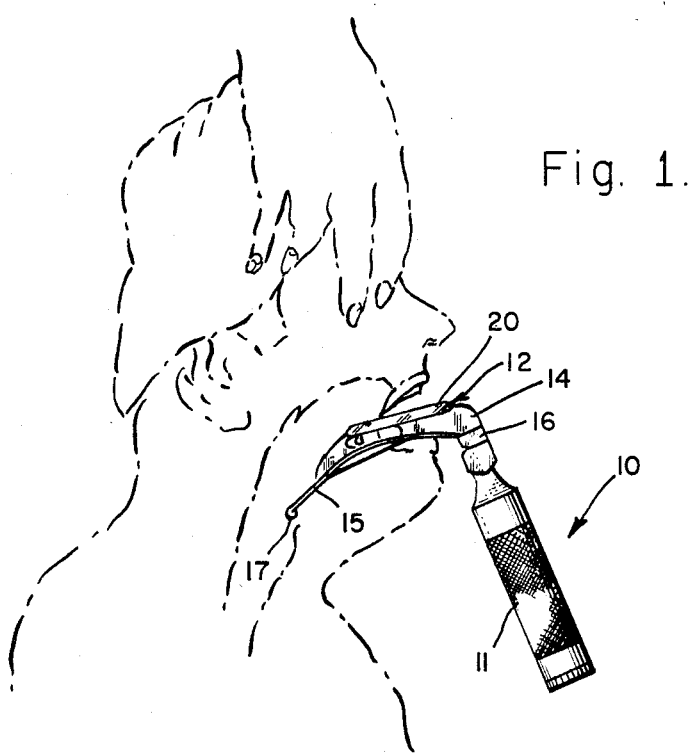
Fig. 1.
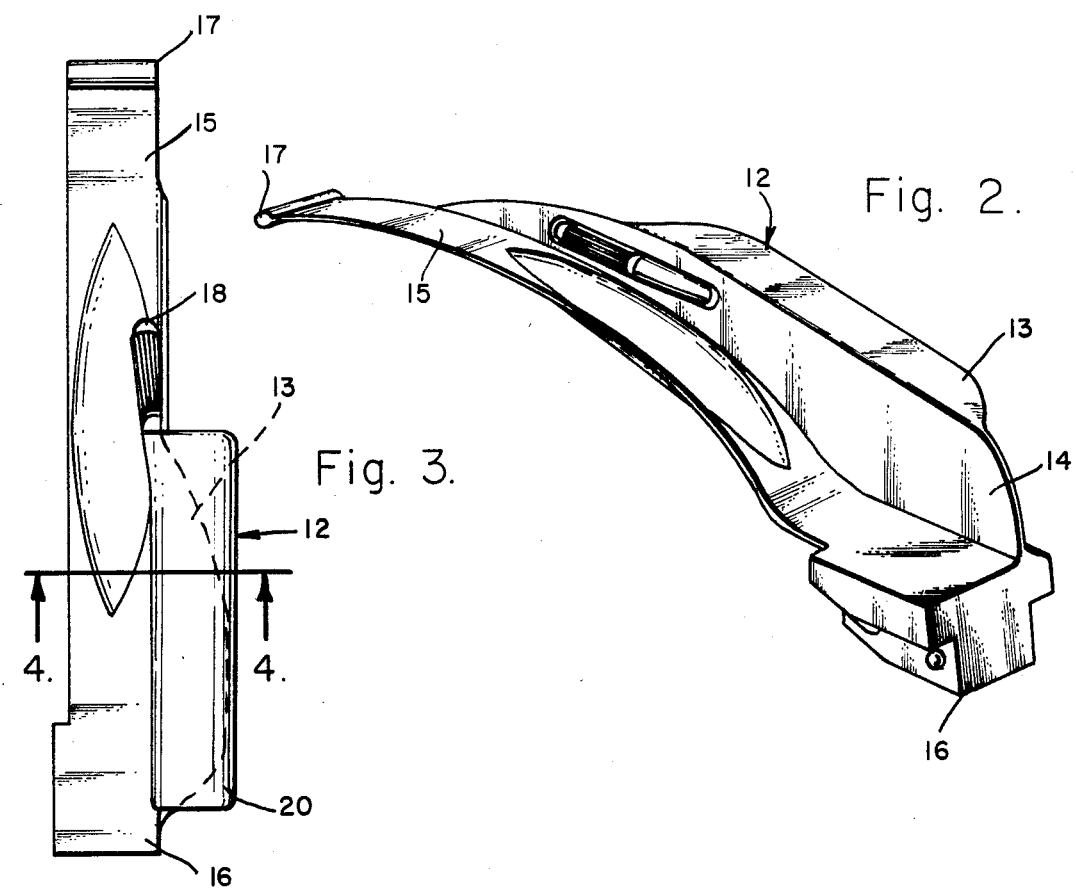
Fig. 2.
Fig. 3.

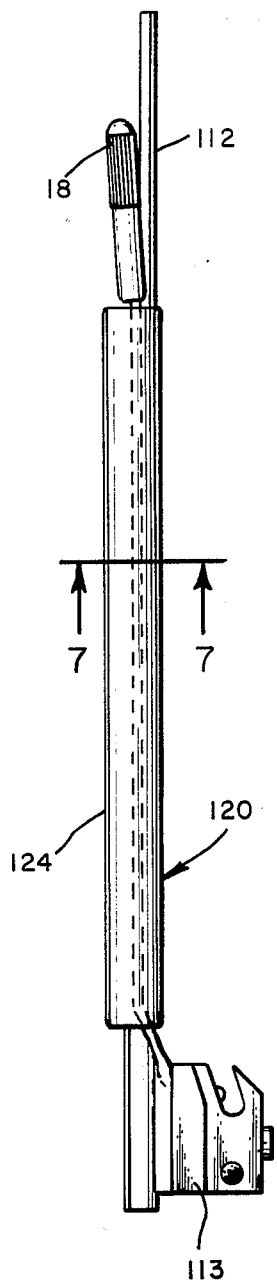
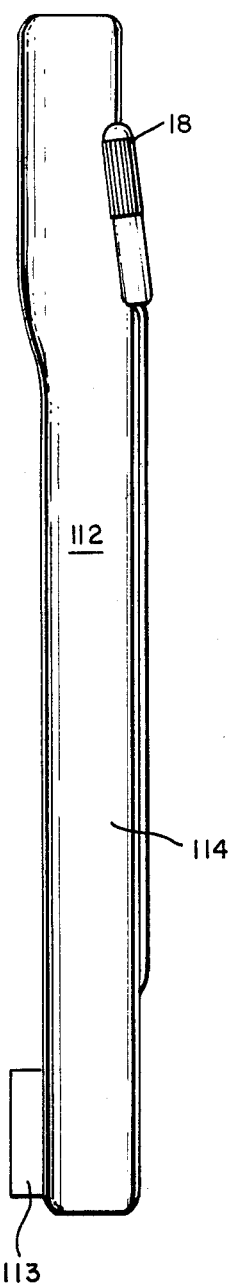
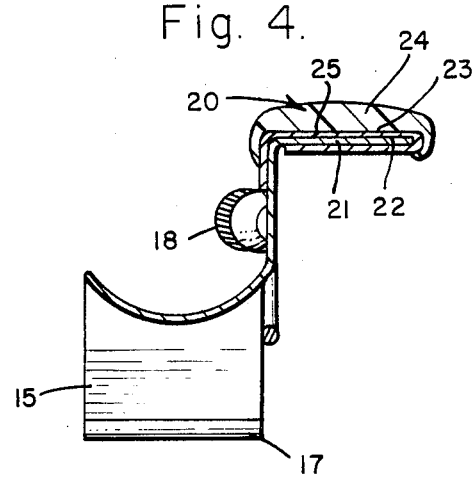
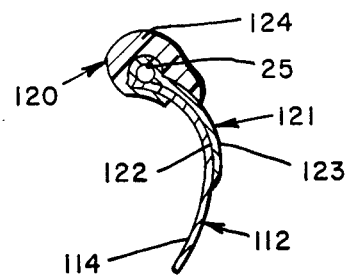

DISPOSABLE CUSHIONING DEVICE FOR A LARYNGOSCOPE

BACKGROUND OF THE INVENTION

1. Field of the Invention

The present invention relates to a laryngoscope and more particularly to a cushioning device for a laryngoscope which is not only sterilizable and disposable, but which also protects the upper teeth of a patient undergoing an endotracheal intubation.

2. Description of the Prior Art

Although there is a risk of possible damage to the upper teeth of patents, laryngoscopes are routinely used to facilitate endotracheal intubation such as during surgery to permit the patients to breathe and/or to administer anesthesia. In addition, laryngoscopes are utilized to displace the tongue and epiglottis thereby permitting direct visualization of the glottis through the mouth opening. The standard method for performing intubation involves placing a patient in a supine position, tilting his head backward as far as possible and distending his lower jaw to open his mouth widely. A rigid blade, which can be straight or slightly curved, then is inserted through his mouth into his throat passageway to displace the tongue and epiglottis thereby exposing the glottis. Thereafter, the desired visual observation can be achieved, the anesthetic can be applied and/or the mechanical ventilation may be effected.

U.S. Pat. No. 4,295,465, entitled Laryngoscope Blade, issued to Gabor Racz and Forrest Allen on Oct. 20, 1981, teaches a blade for a laryngoscope which includes a base portion and projecting flange portion. The flange portion extends along part of the base portion and is pivotally mounted with respect thereto. A biasing mechanism provides a preselected bias force on the flange portion to hold the flange portion in projecting position. If in using the laryngoscope blade the flange portion contacts the patient's upper teeth, the flange porton pivots when the force applied exceeds the predetermined bias force.

U.S. Pat. No. 4,384,570, entitled Laryngoscope, issued to John T. Roberts on May 24, 1983, teaches a laryngoscope which includes a blade and a handle having a rigid handle section and a movable handle section. The movable handle section is adapted to be pivoted and locked at a desired position relative to the rigid handle section prior to use with a patient.

U.S. Pat. No. 4,350,154, entitled Teeth Protecting Device, issued to Elliot V. Feldbau on Sept. 21, 1982, teaches a teeth protecting device which is structured to cling to the teeth with sufficient tenacity so that the teeth protecting device remains secure throughout oral exploration and/or corrective measures and yet so that the teeth protecting device is removable without dislodging pre-existing dental repair work and/or weakly anchored teeth. The provision of mouth-protecting and/or teeth protecting devices for dental, medical and athletic purposes are described in the following patents: U.S. Pat. Nos. 2,705,492, 3,016,052, 3,124,129, 3,236,235, 3,513,838, 3,864,832.

U.S. Pat. No. 3,766,909, entitled Laryngoscope with Disposable Blade and Light Guide, issued to Ahmet M. Ozbey on Oct. 23, 1973, teaches a laryngoscope which includes a wireless, disposable blade containing a relatively stiff light guide for transmitting light from a light source which is associated with the handle to a point substantially midway between the ends of an upper curved section of the disposable blade. The disposable blade is formed of a relatively soft plastic material and has a straight light guide. An adaptor connects the disposable blade to the handle and which mounts the light source in a position adjacent one end of the light guide.

U.S. Pat. No. 3,426,749, entitled Disposable Cover for Laryngoscope Blade, issued to John Anthony Jephcott on Feb. 11, 1969, teaches a disposable cover for a laryngoscope blade. The disposable cover is formed of presterilized, translucent material and is adapted to be pulled over the laryngoscope blade.

U.S. Pat. No. 3,507,272, entitled Laryngoscope, issued to Asmund S. Laerdal on Apr. 21, 1970, teaches a laryngoscope blade which is formed of soft plastic material and upon which a light source is mounted near the distal end of the laryngoscope blade.

U.S. Pat. No. 4,432,350, entitled Means for Applying Topical Anesthesia for Use with a Laryngoscope, issued to Alan J. Breslau and Bernard Broad on Feb. 21, 1984, teaches a laryngoscope which includes a device for applying topical anesthesia.

U.S. Pat. No. 4,437,458, entitled Laryngoscope, issued to Michael S. Upster on Mar. 20, 1984, teaches a laryngoscope which includes a blade which is curved and tubular and which has an improved lighting mechanism for illuminating the forward end of the blade.

U.S. Pat. No. 2,354,471, entitled Laryngoscope, issued to Robert R. MacIntosh on Aug. 18, 1943, teaches a laryngoscope which includes a blade which is curved.

U.S. Pat. No. 2,289,226, entitled Laryngeal Speculum, issued to Richard von Fogregger on July 7, 1942, teaches a laryngoscope which includes a blade which is straight.

U.S. Pat. No. 2,646,036, entitled Foldable and Separable Laryngoscope, issued to William G. Allyn and Charles Sewell Cook on July 21, 1953, teaches a foldable and separable laryngoscope which includes a blade which is straight.

U.S. Pat. No. 4,425,909, entitled Laryngoscope, issued to Michael J. Rieser on Jan. 17, 1984, teaches an improved laryngeal speculum for examining the throat and larynx of a patient. The laryngeal speculum includes an elongated blade, an elongated handle and neck which interconnects the elongated blade and the elongated handle. The neck is shaped, contoured and dimensioned such that when the elongated blade is positioned within the mouth and throat of a patient and lifting force is exerted on the handle there will be no force applied to the upper teeth which have often been used as a fulcrum about which to rotate the handle thereby resulting in numerous broken teeth.

U.S. Pat. No. 4,406,280, entitled Laryngoscope including a Disposable Blade and its Method Use, issued to Michael S. Upster on Sept. 27, 1983, teaches a laryngoscope which includes a separate disposable blade.

U.S. Pat. No. 3,598,113, entitled Disposable Laryngoscope Construction, issued to William C. Moore on Aug. 10, 1971, teaches a disposable laryngoscope which includes a unitary plastic blade and handle assembly which includes a blade portion and a handle portion and which forms a disposable part. The handle portion of the unitary plastic blade and handle assembly is hollow and, when it is in use, contains a light unit which includes batteries, a lamp and an operating switch. The unitary plastic blade and hand assembly includes an optical fiber bundle for carrying light from the lamp within the handle portion to a point near the distal end of the blade portion. The light unit is not disposable and is removed for reuse before the unitary plastic blade and hand assembly is thrown away.

U.S. Pat. No. 3,771,514, entitled Laryngoscope, issued to John P. Huffman and Carl L. Foltz on Nov. 13, 1973, teaches a laryngoscope which allows concurrent direct and indirect viewing of the larynx, especially when direct viewing is difficult. Such indirect viewing is permitted by the use of a prism which is formed out of a plastic material and which also functions as a "bite block".

SUMMARY OF THE INVENTION

In view of the foregoing factors and conditions which are characteristic of the prior art it is the primary object of the present invention to provide a disposable cushioning device for a laryngoscope which protects the upper teeth of a patient undergoing an endotracheal intubation.

It is another object of the present invention to provide a disposable cushioning device for a laryngoscope which is sterilizable.

In accordance with the present invention an embodiment of a disposable cushioning device for a laryngoscope is described. The laryngoscope includes a handle and a blade. The handle contains a battery which is connected to a first electrical contact pad on the upper surface of the handle. The blade has a lateral shelf which has a top surface, an upright wall and a blade portion extending in a direction opposite to the shelf. The blade portion is curved from its base to its tip which is in the form of a rounded transverse bar of the same width as the blade portion. The base of the blade portion is hinged to the top of the handle. The blade carries an electric lamp which is connected to a second electrical contact pad in the base of the blade portion. The disposable cushioning device is sterilizable and includes an elongated sheath which has a bottom surface and a top surface. The elongated sheath is slidably and removably coupled to the shelf of the blade so that the bottom surface is adjacent to the shelf. The disposable cushioning device also includes an elongated layer of soft pliable plastic material. An adhesive material adheres the elongated layer of soft pliable plastic material to the top surface of the elongated sheath. The disposable cushioning device protects the upper teeth of a patient undergoing an endotracheal intubation.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a schematic drawing showing use of a first cushioning device for the blade of a laryngoscope which has been made in accordance with the principles of the present invention and which is not only sterilizable and disposable, but also protects the upper teeth of a patient undergoing an endotracheal intubation.

FIG. 2 is a perspective view of the blade of FIG. 1 having a lateral shelf having a top surface, an upright wall and a blade portion extending in a direction opposite to the shelf wherein the blade portion is curved from its base to its tip.

FIG. 3 is a top plan view of the blade and the first cushioning device of FIG. 1 slidably coupled to the shelf of the blade.

FIG. 4 is a transverse side view in cross-section of the first cushioning device and the shelf of the blade of FIG. 1 taken along line 4—4 of FIG. 3.

FIG. 5 is a top plan of an elongated blade having a base and a curved edge.

FIG. 6 is a elevated side view of a second cushioning device for the blade of a laryngoscope which has been made in accordance with the principles of the present invention and which is not only sterilizable and disposable, but also protects the upper teeth of a patient undergoing an endotracheal intubation wherein the second cushioning device is slidably coupled to the curved edge of the elongated blade of FIG. 5.

FIG. 7 is a transverse side view in cross-section of the second cushioning device of FIG. 6 and the elongated blade of FIG. 5 taken along line 7—7 of FIG. 6.

DESCRIPTION OF THE PREFERRED EMBODIMENT

In order to best understand the present invention it is necessary to refer to the following description of its preferred embodiment in conjunction with the accompanying drawing. Referring to FIG. 1 in conjunction with FIG. 2 a physican uses a first laryngoscope 10 which includes a handle 11 and a blade 12 to perform endotracheal intubation and which is described in U.S. Pat. No. 2,354,471. The handle 11 contains a battery which is connected to a first electrical contact pad on the upper surface of the handle 11. The blade 12 includes a lateral shelf 13, an upright wall 14 and a blade portion 15 which extends in a direction opposite to the shelf 13. The blade portion 15 is curved from its base 16 to of its tip 17, the latter being in the form of a rounded transverse bar of the same width as the blade portion 15. The curvature of the blade portion 15 facilitates easy passage over the tongue and is advantageous in that it avoids depression of the tongue which otherwise might result in an appreciable restriction of the visible aperture of the larynx. The tongue is pushed to one side of the wall 14 and restrained in its movement by the shelf 13. The base 16 of the blade portion 15 is hinged to the top of the handle 11. The blade 12 carries an electric lamp 18 which is connected to a second electrical contact pad in the base 16 of the blade portion 15. When the blade 12 is swung upwards in its operating position the first and second electric contact pads engage to close the circuit through which the electric lamp 18 is lighted in order to illuminate the interior of the mouth.

Referring to FIG. 3 in conjunction with FIG. 4 a first disposable cushioning device 20 is used in combination with the first laryngoscope 10 to protect the upper teeth of a patient undergoing an endotracheal intubation from damage caused by the blade 12. The first disposable cushioning device 20 is sterilizable and includes an elongated sheath 21 which has a bottom surface 22 and a top surface 23. The elongated sheath 21 is slidably and removably coupled to the shelf 13 of the blade 12 so that the bottom surface 22 is adjacent to the shelf 13. The first disposable cushioning device 20 also includes an elongated layer 24 of soft pliable plastic material. An adhesive material 25 adheres the elongated layer 24 of soft pliable material, such as a silicone material or a plastic material, to the top surface 23 of the elongated sheath 21.

Referring to FIG. 5 a second laryngoscope 110 includes a handle 11 and an elongated blade 112 which has a base 113 and a curved edge 114. Referring to FIG. 6 in conjunction with FIG. 7 a second cushioning device 120 is used with the second laryngoscope 110. The second disposable cushioning device 120 includes an elongated sheath 121 which has a bottom surface 122 and a top surface 123 which is slidably and removably coupled to the curved edge 114 of the blade 112 so that said bottom surface 122 is adjacent to the curved edge 114 of the blade 112. The second disposable cushioning device 120 also includes an elongated layer 124 of soft pliable material which is disposed on the entire top surface of the curved edge 114 of the blade 112. An adhesive material 25 adheres the elongated layer 124 of soft pliable material to the top surface 123 of the elongated sheath 121.

From the foregoing it can be seen that a disposable cushioning device for use in combination with a laryngoscope for protecting a patient's upper teeth from damage caused by the blade of the laryngoscope during an endotracheal intubation has been described. It should be noted that the sketches are not drawn to scale and that distance of and between the figures are not to be considered significant.

Accordingly it is intended that the foregoing disclosure and showing made in the drawing shall be considered only as an illustration of the principles of the present invention.

What is claimed is:

1. A disposable cushioning device for use in combination with a laryngoscope which includes a handle containing a battery is connected to a first electrical contact pad on the upper surface of the handle and a blade having a lateral shelf having a top surface, an upright wall and a blade portion extending in a direction opposite to the shelf wherein the blade portion is curved from its base to its tip which is in the form of a rounded transverse bar of the same width as the blade portion, the base of the blade portion is hinged to the top of the handle and the blade carries an electric lamp which is connected to a second electrical contact pad in the base of the blade portion, said disposable cushioning device comprising:

a. an elongated layer of soft pliable material which is disposed on the entire top surface of the shelf of the blade; and
   b. securing means for securing said elongated layer of soft pliable material to the entire top surface of the shelf of the blade whereby said disposable cushioning device protects the upper teeth of a patient undergoing an endotracheal intubation.

2. A disposable cushioning device according to claim 1 wherein said securing means comprises:

a. an elongated sheath having a bottom surface and a top surface which is slidably and removably coupled to the shelf of the blade so that said bottom surface is adjacent to the shelf; and
   b. an adhering means for adhering said elongated layer of soft pliable material to said top surface of said elongated sheath whereby said disposable cushioning device is sterilizable.

3. A cushioning device for use in combination with a laryngoscope which includes a handle containing a battery is connected to a first electrical contact pad on the upper surface of the handle and an elongated blade having a base and a curved edge, the base of the elongated blade is hinged to the top of the handle and the elongated blade carries an electric lamp which is connected to a second electrical contact pad in the base of the blade portion, said disposable cushioning device comprising:

a. an elongated layer of soft pliable material which is disposed on the entire top surface of the curved edge of the blade; and
   b. securing means for securing said elongated layer of soft pliable plastic material to the entire top surface of the curved edge of the blade whereby said disposable cushioning device protects the upper teeth of a patient undergoing an endotracheal intubation.

4. A disposable cushioning device according to claim 3 wherein said securing means comprises:

a. an elongated sheath having a bottom surface and a top surface which is slidably and removably coupled to the curved edge of the blade so that said bottom surface is adjacent to the curved edge of the blade; and
   b. an adhering means for adhering said elongated layer of soft pliable material to said top surface of said elongated sheath whereby said disposable cushioning device is sterilizable.

* * * * *